(12) United States Patent
Moritani

(10) Patent No.: US 10,470,945 B2
(45) Date of Patent: Nov. 12, 2019

(54) METHOD FOR PRODUCING ABSORBENT ARTICLE

(71) Applicant: Daio Paper Corporation, Ehime (JP)

(72) Inventor: Akie Moritani, Ehime (JP)

(73) Assignee: DAIO PAPER CORPORATION, Ehime (JP)

( * ) Notice: Subject to any disclaimer, the term of this patent is extended or adjusted under 35 U.S.C. 154(b) by 384 days.

(21) Appl. No.: 15/124,181

(22) PCT Filed: Feb. 26, 2015

(86) PCT No.: PCT/JP2015/055560
§ 371 (c)(1),
(2) Date: Sep. 7, 2016

(87) PCT Pub. No.: WO2015/146452
PCT Pub. Date: Oct. 1, 2015

(65) Prior Publication Data
US 2017/0014280 A1 Jan. 19, 2017

(30) Foreign Application Priority Data
Mar. 27, 2014 (JP) .................................. 2014-065498

(51) Int. Cl.
*A61F 13/511* (2006.01)
*A61F 13/15* (2006.01)
(Continued)

(52) U.S. Cl.
CPC .. *A61F 13/51104* (2013.01); *A61F 13/15699* (2013.01); *A61F 13/15707* (2013.01);
(Continued)

(58) Field of Classification Search
None
See application file for complete search history.

(56) References Cited

U.S. PATENT DOCUMENTS

2005/0255297 A1 11/2005 Otsuka et al.
2010/0209664 A1 8/2010 Sato et al.
(Continued)

FOREIGN PATENT DOCUMENTS

EP 1419754 A1 5/2004
EP 2687194 A1 1/2014
(Continued)

*Primary Examiner* — Barbara J Musser
(74) *Attorney, Agent, or Firm* — Muncy, Geissler, Olds & Lowe, P.C.

(57) ABSTRACT

A method for producing an absorbent article includes: while conveying non-woven fabric to be a top sheet by drawing from the downstream side, forming extruded projections by embossing; placing a material for a second sheet on the back surface of the non-woven fabric with the extruded projections; and joining the non-woven fabric and material for the second sheet in a joint pattern in which top-second joint portions are formed between the MD direction adjacent extruded projections at CD direction central positions corresponding to CD direction central portions of the adjacent extruded projections and at lateral positions on the CD direction both sides of the central positions. A MD direction joint range of the top-second joint portions is wider continuously or stepwise with increasing proximity from the central position to the lateral sides. This allows joining a top sheet having extruded projections and a second sheet while preventing occurrence of MD direction wrinkles in the top sheet.

3 Claims, 15 Drawing Sheets

(51) Int. Cl.
*A61F 13/56* (2006.01)
*A61F 13/537* (2006.01)
*A61F 13/49* (2006.01)
*B29C 59/04* (2006.01)
*B32B 5/02* (2006.01)
*B32B 7/05* (2019.01)
*B29L 31/48* (2006.01)

(52) U.S. Cl.
CPC .... *A61F 13/49011* (2013.01); *A61F 13/5116* (2013.01); *A61F 13/53743* (2013.01); *A61F 13/5633* (2013.01); *B29C 59/04* (2013.01); *B32B 5/022* (2013.01); *B32B 7/05* (2019.01); *A61F 2013/15715* (2013.01); *B29L 2031/4878* (2013.01)

(56) References Cited

U.S. PATENT DOCUMENTS

2010/0249740 A1* 9/2010 Miyamoto ........ A61F 13/51104
604/384

2012/0226250 A1* 9/2012 Sato .................. A61F 13/51104
604/367
2013/0280481 A1* 10/2013 Mitsuno ............ A61F 13/51121
428/131

FOREIGN PATENT DOCUMENTS

| | | |
|---|---|---|
| JP | 2003306859 A | 10/2003 |
| JP | 2004000466 A | 1/2004 |
| JP | 2005111908 A | 4/2005 |
| JP | 2005245483 A | 9/2005 |
| JP | 2005-314842 A | 11/2005 |
| JP | 2009-000512 A | 1/2009 |
| JP | 2009126107 A | 6/2009 |
| JP | 2009-201964 A | 9/2009 |
| JP | 2010-150686 A | 7/2010 |
| JP | 2011-234896 A | 11/2011 |
| JP | 2014034145 A | 2/2014 |
| WO | WO2011142272 A1 | 11/2011 |

* cited by examiner

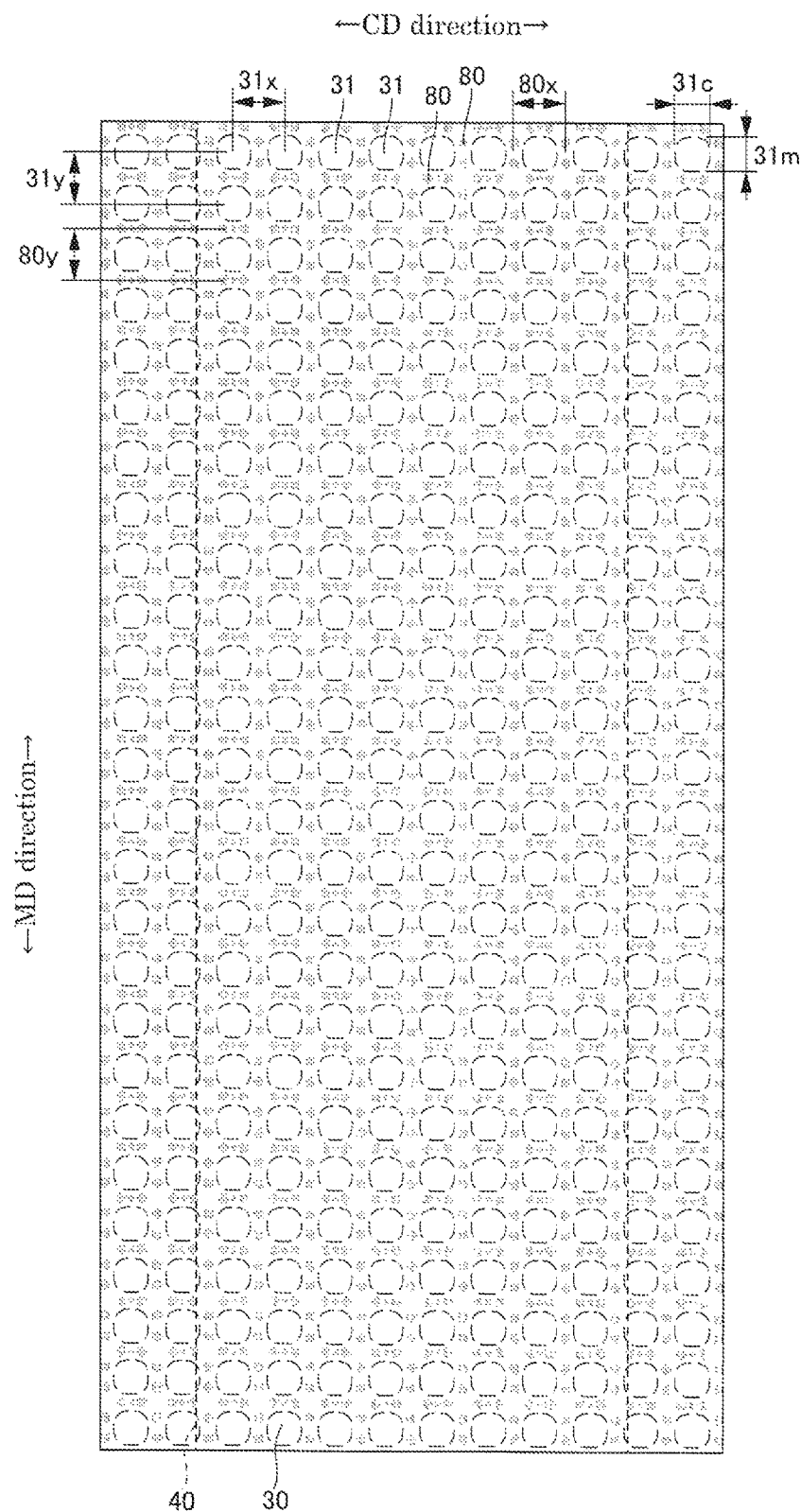

METHOD FOR PRODUCING ABSORBENT ARTICLE

TECHNICAL FIELD

The present invention relates to absorbent articles including disposable diapers and sanitary napkins.

BACKGROUND ART

This kind of absorbent article includes an absorber and a liquid pervious top sheet covering the front side of the absorber so that excrement liquids such as urine and menstrual blood pass through the top sheet and are absorbed and held by the absorber. Conventionally, as top sheets for absorbent articles, non-woven fabric fabricated by various methods, non-woven fabric perforated as secondary processing, porous films made from synthetic resins such as polyethylene, and others have been used. In many absorbent articles, to solve reflowing of excrement liquids from the top sheet to the skin, a second sheet formed from bulky non-woven fabric is stuck to the back surface of the top sheet.

The absorbent articles are required to prevent not only leakage of excretion such as urine but also the wearer's unpleasant feeling, rash, and the like caused by re-sticking of excretion such as urine to the skin. Accordingly, in recent years, in the case of using non-woven fabric for the top sheet, a large number of dome-shaped extruded projections is formed on the top sheet by embossing to decrease the area of contact between the top sheet and the skin, and the portions to be in contact with the skin are softened as described in Patent Documents 1 to 3. In particular, as described in Patent Document 3, when the peripheries of the extruded projections on the top sheet (the bottoms of recesses between the projections) and the second sheet are joined, the extruded projections are more firmly formed and securely maintained even in a pressed state in package bags until they are put to use through distribution process. Such the extruded projections preferably contribute to excellent absorbability and appearance. The embossed top sheet is not only highly functional but also offers beautility to the consumers, and is very important element in appearance as well.

These top sheet and second sheet can be joined at a three-roll processing facility illustrated in FIG. 12, for example. Specifically, the processing facility for the top sheet includes: a push roll 90 with a large number of push convex portions 90a arranged on the peripheral surface; a concave roll 91 that is opposed to the push roll 90, and has concave portions 91a corresponding to the push convex portions 90a and joint convex portions 91b provided between the concave portions 91a; and a joint roll 92 opposed to the concave roll 91. A top sheet material 30S is fed by drawing from the downstream side at a certain tension. The material is first sandwiched between the push roll 90 and the concave roll 91, and the convex portions on the push roll 90 enter into the concave portions 91a on the concave roll 91 to form a large number of extruded projections 31 (protrusions), and then is wound around the concave roll 91. While the material is guided by rotation of the concave roll 91, a second sheet material 40S is fed to the outside of the top sheet material 30S by drawing (extending) from the downstream side at a certain tension. The top sheet material 30S and the second sheet material 40S are sandwiched between the concave roll 91 and the joint roll 92, and are thermally pressed and attached between the joint convex portions 91b of the concave roll 91 and the outer peripheral surface of the joint roll 92, thereby forming top-second joint portions 80.

However, when the article described in Patent Document 3 is produced, a large number of wrinkles is formed along a MD direction (machine direction or sheet conveyance direction) of the top sheet processing facility with space left therebetween in a CD direction (direction orthogonal to the MD direction or transverse direction) as illustrated in FIG. 14(b), thereby leading to a problem of deterioration in appearance.

CITATION LIST

Patent Document

Patent Document 1: JP-A No. 2005-314842
Patent Document 2: JP-A No. 2010-150686
Patent Document 3: JP-A No. 2011-234896

SUMMARY OF INVENTION

Problem to be Solved by the Invention

A major object of the present invention is to join a top sheet having extruded projections and a second sheet while preventing occurrence of MD direction wrinkles in the top sheet.

Means for Solving the Problem

The inventor of the present invention has earnestly studied the wrinkles and revealed that the wrinkles occurring in the top sheet passed through CD direction center of the projections arranged in the MD direction. The inventor has first set up the hypothesis that forming dot-like top-second joint portions at CD-direction central positions corresponding to the CD direction central portions of the MD direction adjacent extruded projections between the adjacent extruded projections would eliminate the excessive wrinkles in the top sheet, but has found this measure to be insufficient for suppressing the occurrence of the wrinkles. Then, the inventor has found out the cause and devised the present invention. The present invention having solved the foregoing problem is as follows:

The Invention of Claim 1

A method for producing an absorbent article including an absorber, a liquid pervious top sheet formed from non-woven fabric covering a front side of the absorber, and a second sheet stuck to a back surface of the top sheet, the top sheet having a large number of extruded projections formed by being extruded from the back side to the front side with space left therebetween in a width direction and a front-back direction, and portions between the extruded projections adjacent in the width direction and the front-back direction in the top sheet being joined to the second sheet to form a large number of top-second joint portions in a joint pattern intermittent in the width direction and the front-back direction, wherein, in assembling the top sheet and the second sheet, the method comprises:

while conveying the non-woven fabric to be the top sheet by drawing from the downstream side, forming the extruded projections by embossing;

placing a material for the second sheet on the back surface of the non-woven fabric with the extruded projections, and joining the non-woven fabric and the material for the second sheet in a joint pattern in which the top-second joint portions are formed between the MD direction adjacent extruded projections at CD direction central positions corresponding to CD direction central portions of the adjacent extruded projections and at lateral positions on the CD direction both sides of the central positions, and a MD direction joint range of the top-second joint portions is wider continuously or stepwise with increasing proximity from the central position to the lateral sides.

(Operation and Effect)

Between the MD direction adjacent extruded projections, the top-second joint portions are formed not only at the CD direction central positions corresponding to the CD direction central portions of the adjacent extruded projection but also at the lateral positions on the CD direction both sides of the central positions. In addition, the non-woven fabric and the second sheet are joined in the joint pattern in which the MD direction joint range of the top-second joint portions is wider continuously or stepwise with increasing proximity from the central positions to the lateral sides. Accordingly, even though vertical wrinkles occur at the time of formation of the extruded projections, the wrinkles can be smoothened out on CD direction both sides and removed or made less prominent without deforming the extruded projections at the time of joining with the second sheet.

The Invention of Claim 2

The method for producing an absorbent article according to claim 1, wherein the top-second joint portions between the MD direction adjacent extruded projections are integral joint portions that extend continuously from the central positions to the CD direction both sides, and become longer continuously or stepwise in the MD direction with increasing proximity to the lateral sides.

(Operation and Effect)

In the present invention, the "joint pattern in which the MD direction joint range of the top-second joint portions is wider continuously or stepwise with increasing proximity from the central positions to the lateral sides" may be formed by the plurality of separated top-second joint portions. However, the integral pattern as described above is more excellent in the effect of preventing occurrence of wrinkles.

The Invention of Claim 3

The method for producing an absorbent article according to claim 1, wherein the top-second joint portions are provided in the central positions and the lateral positions so as to be separated each other, between the MD direction adjacent extruded projections, and the number or length of the top-second joint portions are larger or longer continuously or stepwise in the MD direction with increasing proximity from the central positions to the lateral sides.

(Operation and Effect)

When the "joint pattern in which the MD direction joint range of the top-second joint portions is wider continuously or stepwise with increasing proximity from the central positions to the lateral sides" in the present invention is formed by the integral pattern as described above, there is a possibility of reduction in perviousness and flexibility of the top sheet. However, forming the joint pattern by the plurality of top-second joint portions separated from each other according to claim 3 makes it possible to reduce the possibility and exert fully the effect of preventing wrinkles.

The Invention of Claim 4

The method for producing an absorbent article according to any one of claims 1 to 3, comprising:

using a push roll with a large number of push convex portions formed in an arrangement pattern of the extruded projections on a peripheral surface, a concave roll that is opposed to the push roll, and has concave portions corresponding to the push convex portions and joint convex portions provided between the concave portions, and a joint roll opposed to the concave roll;

while conveying the non-woven fabric to be the top sheet by drawing from the downstream side, sandwiching the non-woven fabric between the push roll and the concave roll, pushing the convex portions in the push roll into the concave portions in the concave roll to form the extruded projections, and then while winding the non-woven fabric to be the top sheet around the concave roll and guiding the same, feeding the material for the second sheet by drawing from the downstream side to the outside of the non-woven fabric to be the top sheet, sandwiching the non-woven fabric to be the top sheet and the material for the second sheet between the concave roll and the joint roll, and thermally pressing and adhering the non-woven fabric to be the top sheet and the material for the second sheet between the joint convex portions of the concave roll and the peripheral surface of the joint roll to form the top-second joint portions.

(Operation and Effect)

According to a producing method by which the extruded projections are joined to the second sheet immediately after the formation of the extruded projections and before the wrinkles are not yet to be substantially absorbed, the wrinkles are more likely to be left. Accordingly, the present invention is preferably applied to such a producing method.

The Invention of Claim 5

An absorbent article, comprising: an absorber; a liquid pervious top sheet formed from non-woven fabric covering the front side of the absorber; and a second sheet stuck to the back surface of the top sheet, the top sheet having a large number of extruded projections formed by being extruded from the back side to the front side with space left therebetween in a width direction and a front-back direction, and portions between the extruded projections adjacent in the width direction and the front-back direction in the top sheet being joined to the second sheet to form a large number of top-second joint portions in a joint pattern intermittent in the width direction and the front-back direction, wherein the top sheet and the second sheet are joined in a joint pattern in which, between the MD direction adjacent extruded projections in the top sheet, the top-second joint portions are formed at least at central positions on a virtual line connecting CD direction central portions of the adjacent extruded projections and at lateral positions on the CD direction both sides of the central positions, and an MD direction joint range is wider continuously or stepwise with increasing proximity from the central positions to the lateral sides.

(Operation and Effect)

The same operation and effect as those of the invention of claim 1 are provided. The terms "MD direction" and "CD direction" in the absorbent article refer to "MD direction" and "CD direction" in the processing facility for the extruded projections, and one of the directions is a front-back direction and the other a width direction. The MD direction in the product is the direction in which fibers of non-woven fabric in the top sheet are oriented. The orientation direction of the fibers is the direction along which the fibers of the non-woven fabric are aligned. The orientation direction can be determined by a measurement method in conformity with a fiber orientation test method with zero-distance tensile strength of TAPPI standard method T481, or a simple measurement method for deciding the direction of fiber orientation from the ratio of tensile strengths in the front-back direction and the width direction, for example.

The Invention of Claim 6

The absorbent article according to claim 5, wherein the top-second joint portions between the MD direction adjacent extruded projections are integral joint portions that extend continuously from the central positions to the CD direction both sides, and become longer continuously or stepwise in the MD direction with increasing proximity to the lateral sides.
(Operation and Effect)
The same operation and effect as those of the invention of claim 2 can be provided.

The Invention of Claim 7

The absorbent article according to claim 6, wherein the top-second joint portions between the MD direction adjacent extruded projections are horizontally-long joint portions longer in the CD direction in which the MD direction length is 0.1 to 1 times as large as MD direction central space in CD direction columns of the MD direction-adjacent extruded projections, and the CD direction length is 0.3 to 1 times as large as than CD direction central space in MD direction columns of the CD direction adjacent extruded projections.
(Operation and Effect)
Although there is no particular limitation, the dimensions of the integral joint portions preferably fall within the scope described in claim 7.

The Invention of Claim 8

The absorbent article according to claim 5, wherein the top-second joint portions are separated into the central positions and the lateral positions between the MD direction adjacent extruded projections, and the number or length of the top-second joint portions are larger or longer continuously or stepwise in the MD direction with increasing proximity from the central positions to the lateral sides.
(Operation and Effect)
The same operation and effect as those of the invention of claim 3 can be provided.

The Invention of Claim 9

The absorbent article according to claim 8, wherein the top-second joint portions between the MD direction adjacent extruded projections are dot-like joint portions in which the MD direction length is 0.1 to 0.4 times as large as MD direction central space in the CD direction columns of the MD direction adjacent extruded projections, and the CD direction length is 0.1 to 0.4 times as large as CD direction central space in the MD direction columns of the CD direction adjacent extruded projections.

(Operation and Effect)
Although there is no particular limitation, the dimensions of the dot-like joint portions preferably fall within the scope described in claim 8.

The Invention of Claim 10

The absorbent article according to any one of claims 5 to 9, wherein a CD direction joint range of the top-second joint portions between the MD direction adjacent extruded projections is 0.3 to 1 times as large as the CD direction central space in the MD direction columns of the CD direction adjacent extruded projections, and
a MD direction joint range of the top-second joint portions between the CD direction adjacent extruded projections is 0.3 to 1 times as large as the MD direction central space in the CD direction columns of the MD direction adjacent extruded projections.
(Operation and Effect)
When the CD direction joint range of the top-second joint portions between the MD direction adjacent extruded projections is too wide, the top-second joint portions are almost continuous in the CD direction, and when the MD direction joint range of the top-second joint portions between the CD direction adjacent extruded projections is too wide, the top-second joint portions are almost continuous in the MD direction, which may lead to reduction in perviousness and flexibility of the top sheet. Accordingly, it is desired to leave sufficient space in the MD direction and the CD direction as described in claim 10.

Advantageous Effects of Invention

As described above, according to the present invention, it is possible to provide an advantage that the top sheet having the extruded projections and the second sheet are joined while preventing the occurrence of wrinkles in the MD direction in the top sheet.

BRIEF DESCRIPTION OF THE DRAWINGS

FIG. 8 is a plane view of a top sheet and a second sheet.

DESCRIPTION OF EMBODIMENTS

Figure 1:
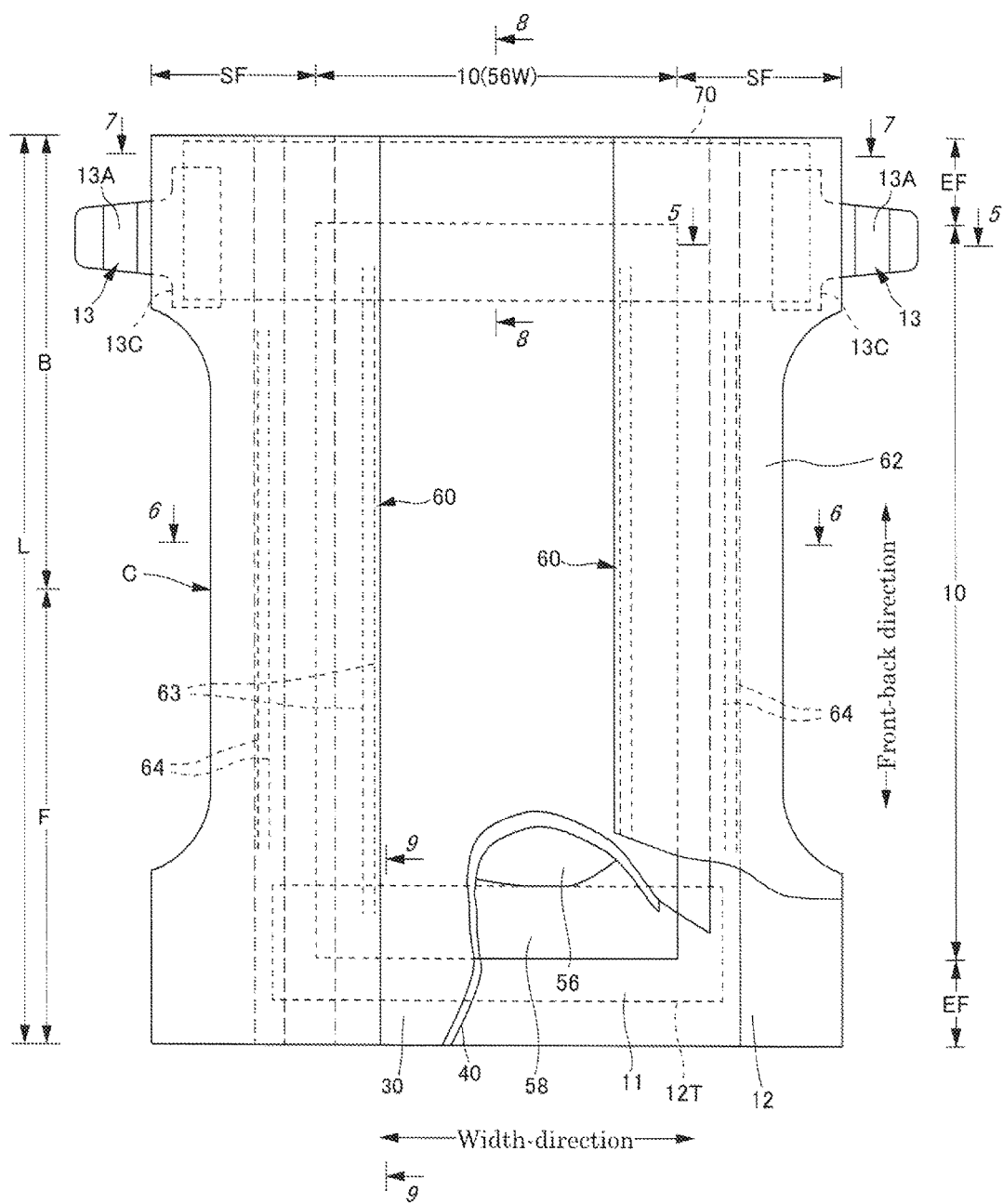
FIG. 1 is a plane view of an inner surface of a tape-type disposable diaper in an opened state.

An embodiment of the present invention will be described below with reference to the accompanying drawings.

FIGS. 1 to 6 illustrate an example of tape-type disposable diaper. In the drawings, reference sign X represents the entire width of the diaper excluding fastening tapes, and reference sign L represents the entire length of the diaper. The constituent members are fixed or joined as necessary even at portions other than fixed portions and joint portions described below, as with publicly known diapers. The means for fixing or joining can be selected as appropriate from among a hot-melt adhesive and welding processes (thermal welding and ultrasonic welding).

The tape-type disposable diaper includes: a liquid pervious top sheet that extends along center in the width direction to cover from an abdominal region through a crotch portion to buttocks and forms a body side surface; an absorbent main body part 10 that has an absorbent element 50 intervening between the absorbent main body part 10 and a liquid impervious sheet positioned on an outer surface side; a ventral side end flap part EF and a dorsal side end flap part EF that extend at the front and back sides of the absorbent main body part 10 and do not have the absorbent element 50.

The tape-type disposable diaper also has a pair of side flap parts SF and SF that extends at the lateral sides beyond the side edges of the absorbent main body part 10 and fastening tapes 13 on dorsal sides of the side flap parts SF and SF.

More specifically, the entire outer surfaces of the absorbent main body part 10 and the side flap parts SF and SF are formed from an outer sheet 12. In particular, in the absorbent main body part 10, a liquid impervious sheet 11 is fixed to the inner surface side of the outer sheet 12 by an adhesive such as a hot-melt adhesive, and the absorbent element 50, a second sheet 40, and a top sheet 30 are layered in this order on the inner surface side of the liquid impervious sheet 11. The top sheet 30 and the liquid impervious sheet 11 are rectangular in shape in the illustrated example. The top sheet 30 and the liquid impervious sheet 11 are slightly larger in dimensions than the absorbent element 50 in the front-back direction and in the width direction, and a peripheral edge portion of the top sheet 30 extending off the absorbent element 50 and a peripheral edge portion of the liquid impervious sheet 11 extending off the absorbent element 50 are adhered to each other by a hot-melt adhesive or the like. The liquid impervious sheet 11 is made from a moisture-pervious polyethylene film or the like and is slightly wider than the top sheet 30.

Further, side-part three-dimensional gathers 60 and 60 are provided on the both sides of the absorbent main body part 10 so as to protrude (stand) toward the skin of the wearer. Gather sheets 62, 62 constituting the side-part three-dimensional gathers 60 and 60 are fixed and adhered in a range from the above of the both sides of the top sheet 30 to the inner surfaces of the side flap parts SF and SF.

The materials and features of the respective parts will be described in sequence below.

(Outer Sheet)

The outer sheet 12 is a part to support the absorbent element 50 to be attached to the wearer. The outer sheet 12 has an hourglass-like shape that is narrowed at a middle portion in the front-back direction on the both sides to surround the legs of the wearer.

The outer sheet 12 is preferably non-woven fabric but is not limited to this. There is no particular limitation on the kind of non-woven fabric. For example, the fibers of the material may be synthetic fibers based on olefin such as polyethylene or polypropylene, polyester, polyamide, or reproduced fibers such as rayon or cupra, natural fibers such as cotton, or the like and the processing method may be spun-lacing, spun-bonding, thermal bonding, air-through processing, and needle-punching, or the like. However, for the compatibility between texture and strength, long-fibered non-woven fabrics such as spun-bonded non-woven fabric, SMS non-woven fabric, and SMMS non-woven fabric are preferred. The non-woven fabric may be used as a single sheet or an overlapped layer of two or more sheets. In the latter case, the sheets of non-woven fabric are preferably adhered to each other by a hot-melt adhesive or the like. In the case of using non-woven fabric, the basis weight of fibers is desirably 10 to 50 $g/m^2$, in particular 15 to 30 $g/m^2$.

(Liquid Impervious Sheet)

There is no particular limitation on the material for the liquid impervious sheet 11. For example, however, the material may be an olefin resin such as polyethylene or polypropylene, a laminate non-woven fabric sheet in which non-woven fabric is stacked on a polyethylene sheet or the like, a non-woven fabric sheet in which a waterproof sheet intervenes to secure substantially liquid imperviousness (in this case, the waterproof sheet and the non-woven fabric constitute a liquid impervious sheet), or the like. As a matter of course, other liquid impervious and moisture-pervious materials having been used preferably in recent years from the viewpoint of stuffiness prevention may be used. The liquid impervious and moisture-pervious material sheet may be a microporous sheet that is obtained by melting and kneading an inorganic filling agent in an olefin resin such as polyethylene, polypropylene, or the like, for example, to form a sheet and then elongating the sheet in a uniaxial or biaxial direction. Besides, the liquid impervious sheet 11 may be a non-woven fabric sheet of microdenier fibers, or may be a liquid impervious sheet that is formed without the use of a waterproof film, by enhancing leak-proof performance by reducing the size of air gaps between fibers with the application of heat or pressure or by coating the sheet with a high-water absorption resin, a hydrophobic resin, or a water repellent agent.

(Top Sheet)

The top sheet 30 is pervious to liquid and may be a porous or non-porous non-woven fabric. There is no specific limitation on raw fibers for the non-woven fabric. For example, the raw fibers may be synthetic fibers based on olefin such as polyethylene and polypropylene, polyester, or polyamide, reproduced fibers of rayon, cupra, or the like, natural fibers of cotton or the like, and mixed fibers or composite fibers of two or more of the foregoing fibers. The non-woven fabric may be produced by any processing method. The processing method may be any of publicly known methods such as spun-lacing, spun-bonding, thermal bonding, melt-blowing, needle-punching, air-through processing, and point-bonding, for example. For flexibility and drape properties, spun-lacing is preferred. For bulkiness and softness, thermal bonding is preferred.

The top sheet 30 may be composed of a single sheet or a layered sheet obtained by sticking two or more sheets to each other. Similarly, the top sheet 30 may be composed of a single sheet or two or more sheets in a planar direction.

(Second Sheet)

The second sheet 40 is joined to the back surface of the top sheet 30 to move the excrement liquid having passed through the top sheet 30 quickly to the absorber 56 and prevent reflowing of the excrement liquid. In the case of using heat embossing or ultrasonic welding to join the second sheet 40 to the top sheet 30, the material for the second sheet 40 has preferably a fusing point to the same level as the top sheet 30. The second sheet 40 may be non-woven fabric or a resin film with a large number of permeable pores. The non-woven fabric for the second sheet 40 may be the same as the non-woven fabric for the top sheet 30 described above. However, the non-woven fabric for the second sheet 40 is preferably higher in hydrophilic property and fiber density than the non-woven fabric for the top sheet 30 so that the transfer property of the liquid from the top sheet 30 to the second sheet 40 is more excellent.

The second sheet 40 in the illustrated example is smaller in width than the absorbent element 50 and is arranged at the center of the absorbent element 50. Alternatively, the second sheet 40 may be provided over the entire width of the absorbent element 50. The front-back direction length of the second sheet 40 may be equal to the entire length of the diaper, may be equal to the length of the absorbent element 50, or may fall within a short range centered on the region for receiving the liquid.

(Side-Part Three-Dimensional Gathers)

The side-part three-dimensional gathers 60, 60 are preferably provided so as to protrude (stand) toward the usage surface on the both sides of the product to shut off urine or loose stool moving laterally over the top sheet 30 to prevent lateral leakage of the liquid.

Figure 3:
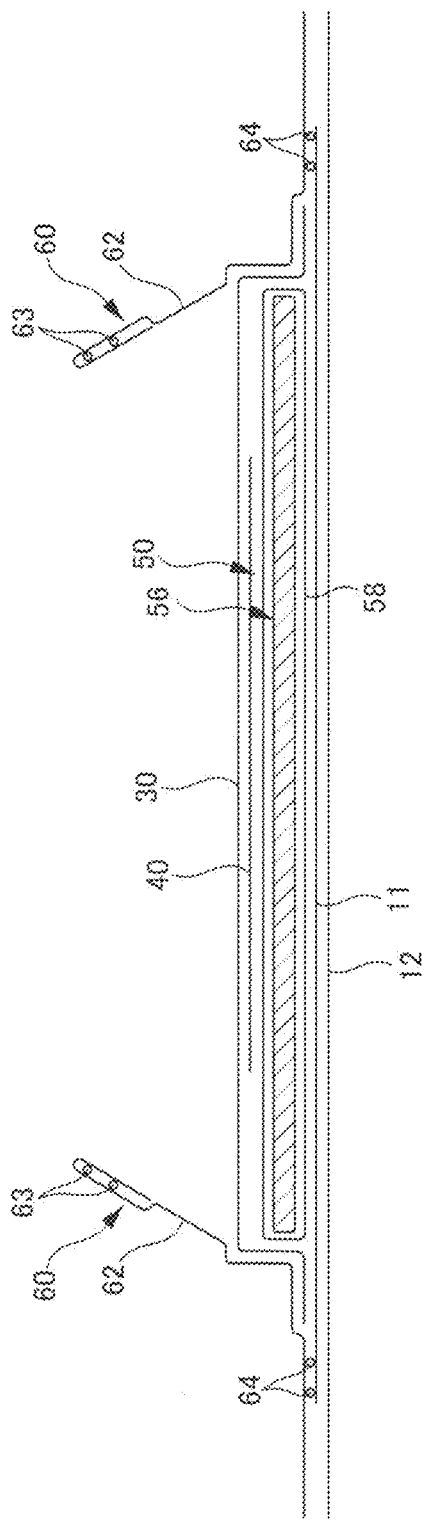
FIG. 3 is a cross-sectional view of FIG. 1 along line 6-6.
Figure 4:
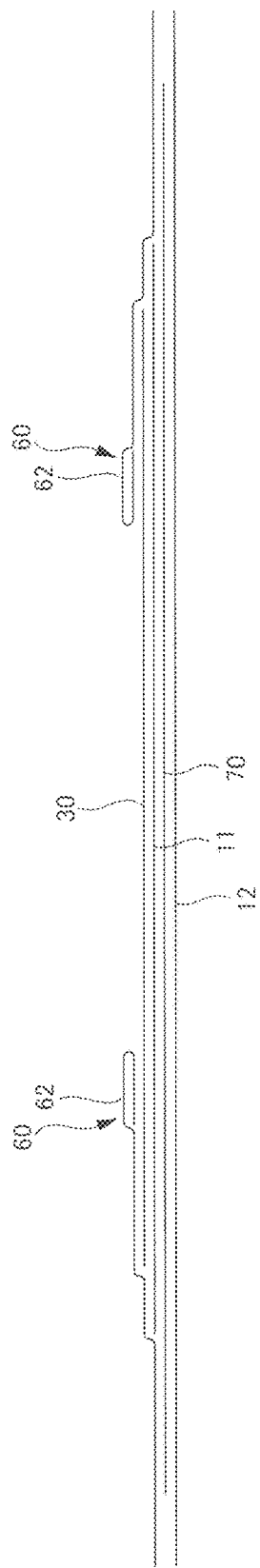
FIG. 4 is a cross-sectional view of FIG. 1 along line 7-7.

The side-part three-dimensional gather 60 is composed of the gather sheet 62 that is continuous substantially in the width direction and an elongated resilient and elastic member 63 that is fixed in an extended state to the gather sheet 62 along the front-back direction. The gather sheet 62 may be water-repellent non-woven fabric, and the resilient and elastic member 63 may be rubber thread or the like. The number of the provided resilient and elastic member may be plural as illustrated in FIGS. 1 and 3 or may be one in each sheet.

The inner surface of the gather sheet 62 has a fixation starting end in the width direction above the side part of the top sheet 30. An outer part of the fixation starting end in the width direction is fixed and adhered by a hot-melt adhesive or the like to a side part of the liquid impervious sheet 11 as well as a side part of the outer sheet 12 positioned on the outside of the side part of the liquid impervious sheet.

Around the legs, the inner side in the width direction of the fixation starting end of the side-part three-dimensional gather 60 is fixed to the top sheet 30 on both front end and back end in the front-back direction of the product, but a part between the front end and the back end are non-fixed free portion. The free portion is stood by contraction force of the resilient and elastic member 63. When the diaper is worn, the diaper is attached in a boat-like shape to the body of the wearer. Then, the contraction force of the resilient and elastic member 63 acts to allow the side-part three-dimensional gather 60 to stand and attach closely to the leg. As a result, it is possible to prevent lateral leakage around the leg.

Unlike the illustrated example, the both ends in the front-back direction of the inner part in the width direction of the gather sheet 62 may be fixed in a two-fold state having a base side end portion, which extends from the outer part in the width direction to the inside in the width direction, and a forward portion, which is folded back from the center side edge in the width direction of the base side end portion toward the wearer's body side and then which extends outside in the width direction. The portion between the front end and the back end may be non-fixed free portion.

(Plane Gather)

Figure 2:
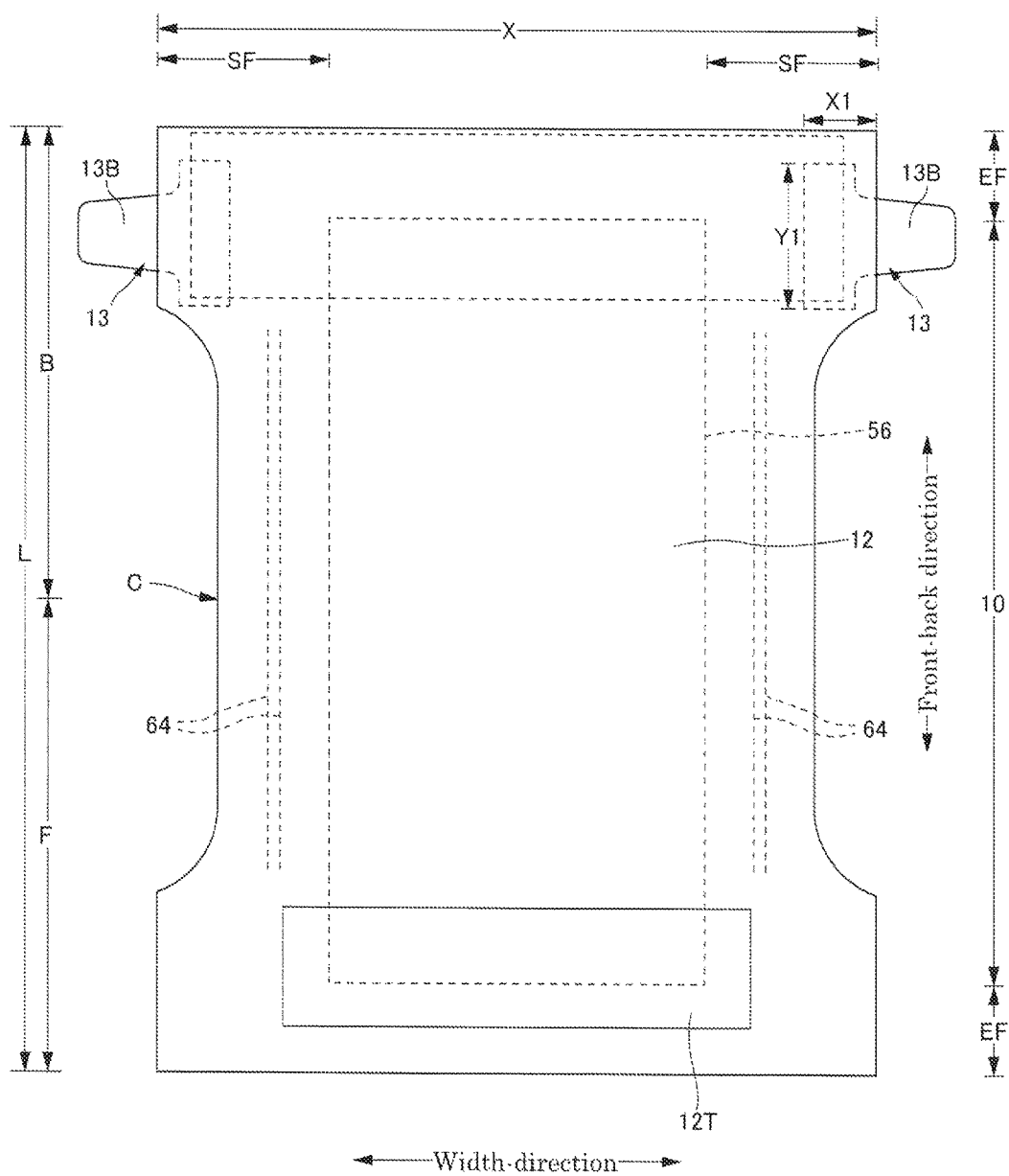
FIG. 2 is a plane view of an outer surface of the tape-type disposable diaper in the opened state.

In each of side flaps SF, SF, resilient and elastic members 64 formed from rubber thread or the like are fixed in an extended state along the front-back direction between the gather sheet 62 and the liquid impervious sheet 11 on the outside in the width direction of the fixed and adhered portion of the gather sheet 62 near the fixation starting end as illustrated in FIGS. 1 to 3. Accordingly, the portion of each of the side flap parts SF, SF around the leg is formed as a plane gather. The leg resilient and elastic members 64 may be arranged between the liquid impervious sheet 11 and the outer sheet 12 on the side flap part SF. The number of the leg resilient and elastic member 64 may be plural on each of the sides in the illustrated example or may be one on each of the sides.

(Absorbent Element)

The absorbent element 50 is a part that absorbs and holds liquids such as urine or loose stool. The absorbent element 50 has an absorber 56 and a wrapping sheet 58 wrapping at least the back surface and side surfaces of the absorber 56. The wrapping sheet 58 may be omitted. The absorbent element 50 can be adhered at the back surface to the inner surface of the liquid impervious sheet 11 by an adhesive such as a hot-melt adhesive.

(Absorber)

The absorber 56 may be formed from a fiber assembly. The fiber assembly may be fluff pulp fibers or accumulated short fibers such as synthetic fibers, or a filament assembly obtained by opening tows (fiber bundles) of synthetic fibers such as cellulose acetate, as necessary. The basis weight of fluff pulp or accumulated short fibers may be about 100 to 300 g/m$^2$, and the basis weight of a filament assembly may be about 30 to 120 g/m$^2$, for example. The fineness of synthetic fibers is, for example, 1 to 16 dtex, preferably 1 to 10 dtex, more preferably 1 to 5 dtex. In the case of a filament assembly, the filaments may be non-crimped fibers but are preferably crimped fibers. The number of crimps in the crimped fibers may be, for example, about 5 to 75 per inch, preferably about 10 to 50 per inch, more preferably about 15 to 50 per inch. The crimped fibers are evenly crimped in many cases.

(High Absorbent Polymer Particles)

The absorber 56 preferably includes high absorbent polymer particles, and in particular, desirably has high absorbent polymer particles (SAP particles) dispersed in the assembly of fibers in the substantially entire thickness direction at least in a liquid receiving region.

When there are no or few SAP particles in the upper, lower, and middle parts of the absorber 56, it cannot be said that the SAP particles are "dispersed in the entire thickness direction". Therefore, the form in which the SAP particles are "dispersed in the entire thickness direction" includes the form in which the SAP particles are "evenly" dispersed in the assembly of fibers in the entire width direction, and the form in which the SAP particles are "unevenly distributed" in the upper, lower, and middle parts but still dispersed in the upper, lower, and middle parts. In addition, the form in which the SAP particles are dispersed in the entire thickness direction does not exclude the form in which some of the SAP particles remain on the surface of the assembly of fibers without entering into the assembly of fibers or the form in which some of the SAP particles pass through the assembly of fibers and reside on the wrapping sheet 58.

The high-absorbent polymer particles include "powders" as well as "particles". The diameter of the high-absorbent polymer particles 54 may be the same as that of particles for general use in this type of absorbent article and preferably 1000 μm or less, more preferably 150 to 400 μm. There is no particular limitation on the material for the high-absorbent polymer particles but the material preferably has a water absorption capacity of 40 g/g or more. The high-absorbent polymer particles may be based on starch, cellulose, or synthetic polymer. The high-absorbent polymer particles may be made of a starch-acrylic acid (salt) graft copolymer, a saponified material of starch-acrylonitrile copolymer, a crosslinking substance of carboxymethyl-cellulose sodium, an acrylic acid (salt) polymer, or the like. The high-absorbent polymer particles are preferably used in a general particulate form but may be used in another form.

The water absorption rate of the high-absorbent polymer particles is preferably 40 seconds or less. At a water absorption rate of more than 40 seconds, the absorbed liquid is more likely to flow back from the absorber 56 to the outside of the absorber 56 (so called "reflowing").

The basis weight of the high absorbent polymer particles can be decided as appropriate depending on the absorption volume required in the use of the absorber 56. Therefore, although being not specified absolutely, the basis weight may be 50 to 350 g/m$^2$. When the basis weight of the polymer is lower than 50 g/m$^2$, it is hard to assure the absorption volume. When the basis weight of the polymer exceeds 350 g/m$^2$, the effect becomes saturated and the excessive amount of high absorbent polymer particles causes gritty and uncomfortable feeling.

(Wrapping Sheet)

In the case of using the wrapping sheet 58, the material thereof may be tissue paper, in particular, crape paper, non-woven fabric, polyethylene-laminated non-woven fabric, a porous sheet, or the like. However, the material sheet is desirably configured to retain the high-absorbent polymer particles. In the case of using non-woven fabric instead of crape paper, the hydrophilic SMMS non-woven fabric (spun-bonded/melt-blown/melt-blown/spun-bonded) is preferred in particular and its material may be polypropylene, polyethylene/polypropylene, or the like. The basis weight of the material is desirably 5 to 40 g/m$^2$, in particular 10 to 30 g/m$^2$.

The wrapping sheet 58 may wrap the entire absorber 56 as illustrated in FIG. 3 or may wrap only the back surface and side surfaces of the absorber 56. In addition, although not illustrated, only the upper surface and side surfaces of the absorber 56 may be covered with crepe sheet or non-woven fabric and the lower surface of the same may be covered with a liquid impervious sheet of polyethylene or the like, or the upper surface of the absorber 56 may be covered with crepe paper or non-woven fabric and the side surfaces and the lower surface of the absorber 56 may be covered with a liquid impervious sheet of polyethylene or the like (these materials are constituent elements of the wrapping sheet). If necessary, the absorber 56 may be sandwiched between the two upper and lower sheets or may be arranged on the lower surface. However, these forms are not desired because they make it difficult to prevent the movement of the high absorbent polymer particles.

(Fastening Tapes)

Figure 7:
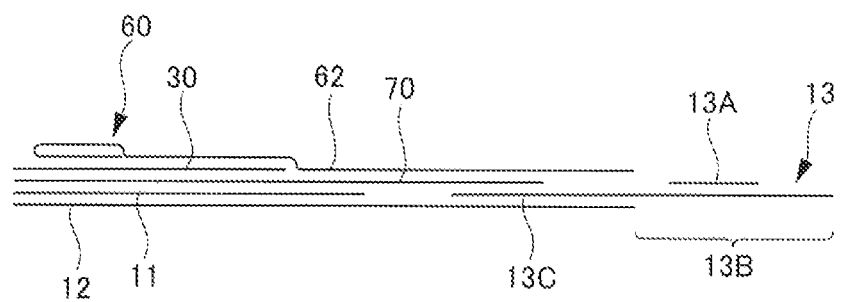
FIG. 7 is a cross-sectional view of FIG. 1 along line 5-5.

As illustrated in FIGS. 1, 2, and 7, the fastening tapes 13 each include a tape attachment part 13C fixed to the side part of the diaper, a sheet base material forming a tape main part 13B and protruding from the tape attachment part 13C, and an engage part 13A that is provided relative to the ventral side in the width-direction intermediate portion of the tape main part 13B in the sheet base material. The tip of the fastening tape 13 beyond the engage part 13A constitutes a tab. The tape attachment part 13C of the fastening tape 13 is sandwiched between the gather sheet 62 as inner layer in the side flap part and the outer sheet 12 as outer layer in the side flap part, and is attached to the both sheets 62 and 12 by a hot-melt adhesive. The engage part 13A is joined to the sheet base material by an adhesive in a manner incapable of being separated.

For a diaper for infants, out of the dimensions of the tape attachment part 13C, a diaper width-direction length X1 is preferably 10 to 50 mm, in particular, 20 to 40 mm, and a diaper front-back direction length Y1 is preferably 20 to 100 mm, in particular, 40 to 80 mm. In addition, out of the dimensions of the tape main part 13B, a diaper width-direction length is preferably 30 to 80 mm, in particular, 40 to 60 mm, and a diaper front-back direction length (height) is preferably 20 to 70 mm, in particular, 25 to 50 mm. When the fastening tape 13 is partially or entirely almost tapered and the front-back direction length and the width direction length are not uniform, the foregoing ranges of numeric values are decided by average values. The shape of the fastening tape 13 may be symmetric such as a rectangle. However, the fastening tape 13 preferably has a convex shape formed by a wide attachment portion and a narrow tip portion because the tab of the tip portion is easier to pick up and tensile force acts widely between the right and left base portions.

The engage part 13A is preferably a hook material (male material) of a mechanical fastener (surface fastener). The hook material has a large number of engage protrusions on the outer surface. The shape of the engage protrusions may be any one of (A) checkmark shape, (B) J shape, (C) mushroom shape, (D) T shape, (E) double-J shape (two Js joined back to back), and others. As a matter of course, the engage part of the fastening tape 13 may be a gluing agent layer.

The sheet base material for forming the tape attachment part to the tape main part may be non-woven fabric, plastic film, polyethylene-laminated non-woven fabric, paper, or a composite of these materials. Preferably, the sheet base material is spun-bonded non-woven fabric, air-through non-woven fabric, or spun-laced non-woven fabric with a fineness of 1.0 to 3.5 dtex, a basis weight of 20 to 100 g/m$^2$, and a thickness of 1 mm or less.

To put on the diaper, the dorsal side side flap parts SF are overlapped with the outer side of the ventral side side flap parts SF, and the fastening tapes are engaged at appropriate sites on the outer surface of the ventral side F. The engage positions and dimensions of the fastening tapes 13 can be arbitrarily decided. For a diaper for infants, each of the engage sites preferably falls within a rectangular area of 20 to 80 mm in the front-back direction and 150 to 300 mm in the width direction. The height-direction separation distance between the upper end edge and the ventral side upper edge of the rectangular area is preferably 0 to 60 mm, in particular 20 to 50 mm, and the rectangular area preferably resides at the width-direction center of the product.

The fastening tapes 13 are preferably attached such that the tape attachment parts 13C of the fastening tapes 13 overlap at the boundaries between the dorsal side end flap parts EF and the absorbent element 50 because the dorsal side end part of the absorbent element 50 is firmly pressed against the body of the wearer by tensile force acting between the attachment parts of the right and left fastening tapes 13 when the diaper is worn. In addition, when the attachment parts of the fastening tapes 13 are too separated from the dorsal side end part (back end part) of the diaper, the tensile force acting between the tape attachment parts 13C of the right and left fastening tapes 13 does not exert on the dorsal side end part of the diaper when the diaper is worn, whereby a gap is likely to occur between the dorsal side end part of the diaper and the body surface of the wearer. Therefore, the front-back direction length of the dorsal side end flap parts EF is preferably equal to or smaller than the front-back direction length of the tape attachment parts 13C of the fastening tapes 13.

(Target Sheet)

Target sheet 12T having targets for facilitating the engagement are preferably provided on the ventral side F at the engage sites of the fastening tapes 13. When the engage parts are hook materials 13A, the target sheet 12T may be formed by providing a large number of thread loops to be entangled with engage protrusions of the hook materials on the surface of a sheet base material made from a plastic film or non-woven fabric. When the engage parts are gluing material layers, the target sheet 12T may be formed by applying a separation treatment to the surface of a sheet base material made from a smooth plastic film with glutinosity. In addition, when the engage sites of the fastening tapes 13 on the ventral side F are made from non-woven fabric, for example, when the outer sheet 12 in the illustrated example is made from non-woven fabric and the engage parts of the fastening tapes 13 are hook materials 13A, the target sheet 12T may not be provided but the hook materials 13A may be entangled and engaged with the non-woven fabric of the outer sheet 12. In this case, the target sheet 12T may be provided between the outer sheet 12 and the liquid impervious sheet 11.

(End Flap Parts)

The end flap parts EF extend to the front side and the back side of the absorbent main body part 10 and do not have the absorbent element 50. The extension part of the front side is a ventral side end flap part EF, and the extension part of the back side is a dorsal side end flap part EF.

The front-back direction length of the dorsal side end flap EF is preferably equal to or smaller than the front-back direction length of the attachment parts of the fastening tapes 13 for the reason described above. When the dorsal side end part of the diaper and the absorbent element 50 are too close to each other, a gap is likely to occur between the dorsal side end part of the diaper and the body surface of the wearer due to the thickness and resilience of the absorbent element 50. Accordingly, the front-back direction length of the dorsal side end flap EF is preferably 10 mm or more.

The front-back direction length of the ventral side end flap part EF and the dorsal side end flap part EF is preferably about 5 to 20% of the front-back direction length L of the entire diaper. For a diaper for infants in particular, the front-back direction length of the ventral side end flap part EF and the dorsal side end flap part EF is appropriately 10 to 60 mm, specifically 20 to 50 mm.

(Dorsal Side Elastic Waist Sheet)

Figure 5:
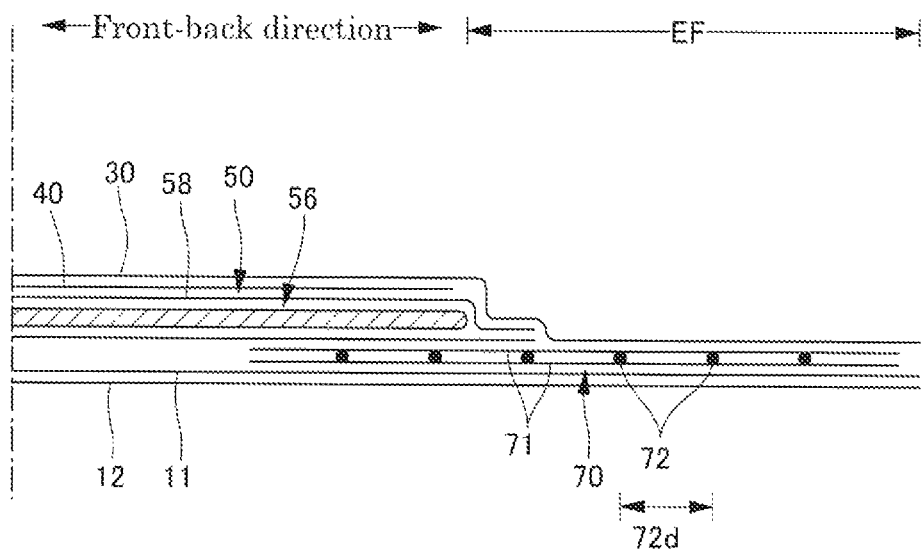
FIG. 5 is a cross-sectional view of FIG. 1 along line 8-8.
Figure 6:
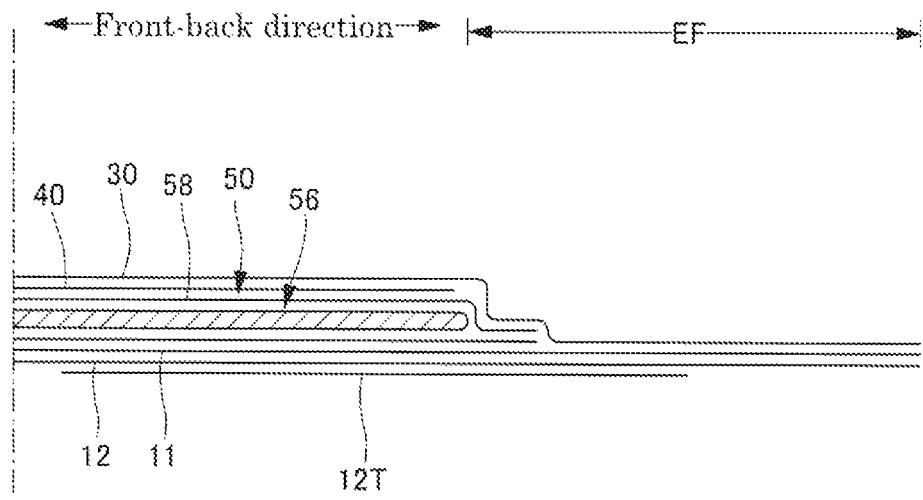
FIG. 6 is a cross-sectional view of FIG. 1 along line 9-9.

In the illustrated example, a belt-like dorsal side elastic waist sheet 70 elastically stretching in the width direction is provided between the fastening tapes 13 to improve a fit at the dorsal side part of the diaper. The both ends of the dorsal side elastic waist sheet 70 are preferably extended to the sites overlapping the attachment parts of the fastening tapes 13, but may be separated from the attachment parts of the fastening tapes 13 on the width-direction central side. The front-back direction dimension of the dorsal side elastic waist sheet 70 is appropriately equal to the front-back direction dimension of the attachment parts of the fastening tapes 13, but may have a dimension difference of about ±20% from the front-back direction dimension of the attachment parts of the fastening tapes 13. In addition, the dorsal side elastic waist sheet 70 preferably overlaps the boundaries between the dorsal side end flap parts EF and the absorbent element 50 as illustrated in the drawing because the dorsal side end of the absorbent element 50 can be firmly pressed against the body of the wearer. The dorsal side elastic waist sheet 70 may be a sheet-like resilient member such as a rubber sheet, but is preferably made from non-woven fabric or paper from the viewpoint of air permeability. In this case, a sheet-like resilient member with air permeability such as elastic non-woven fabric may be used. However, as illustrated in FIG. 5, the dorsal side elastic waist sheet 70 is preferably formed by sticking two sheet base materials 71 of non-woven fabric or the like by an adhesive such as a hot-melt adhesive and fixing sheet-like, net-like, or elongated (thread-like or string-like) porous resilient and elastic members 72 in an extended state along the width direction between the sheet base materials 71. In this case, the sheet base materials 71 may be the same as the outer sheet 12. The extension ratio of the resilient and elastic members 72 is preferably about 150 to 250%. In addition, in the case of the elongated (thread-like or string-like) resilient and elastic members 72, about 5 to 15 resilient and elastic members 72 with a thickness of 420 to 1120 dtex are preferably provided at spaces 72d of 3 to 10 mm.

Some of the resilient and elastic members 72 may be preferably arranged across the absorbent element 50 to improve a fit of the absorbent element 50. Nevertheless, in this case, some or all of the resilient and elastic members 72 overlapping the absorbent element 50 are treated by means such as cutting so as not to exert contraction force because the dorsal side end part of the absorbent element 50 does not contract in the width direction, thereby further improving a fit.

The resilient and elastic members 72 may be fixed over the entire length of the sheet base materials 71 along the longitudinal direction of the sheets (diaper width direction). However, for prevention of shrinkage or roll-up of the sheet base materials 71 when being attached to the diaper main body, the resilient and elastic members 72 are treated so as not to exert contraction force, or are not provided within a range of about 5 to 20 mm at the front-back ends of the sheets (diaper width direction).

In the illustrated example, the dorsal side elastic waist sheet 70 is sandwiched between the gather sheets 62 and the outer sheet 12 on the width-direction both sides of the liquid impervious sheet 11, and is sandwiched between the liquid impervious sheet 11 and the absorbent element 50 at a site overlapping the liquid impervious sheet 11. Alternatively, the dorsal side elastic waist sheet 70 may be provided between the liquid impervious sheet 11 and the outer sheet 12, may be provided on the outer surface of the outer sheet 12, or may be provided between the top sheet 30 and the absorbent element 50. In addition, the dorsal side elastic waist sheet 70 may be provided on the top sheet 30. In this case, the dorsal side elastic waist sheet 70 may be provided on the gather sheets 62 on the width-direction both sides of the liquid impervious sheet 11. In the case of forming the outer sheet 12 by overlapping a plurality of sheet base materials, the entire dorsal side elastic waist sheet 70 may be provided between the sheet base materials of the outer sheet 12.

(Extruded Projections on the Top Sheet)

A large number of extruded projections 31 formed by extruding the top sheet 30 from the back side to the front side by embossing is arranged with spaces therebetween on the top sheet 30 in the width direction and the front-back direction. The arrangement form may be a matrix form as illustrated in FIGS. 8 and 9 or may be a staggered form (alternate arrangement between adjacent columns) as illustrated in FIG. 10.

The dimensions and the like of the extruded projections 31 can be decided as appropriate. However, an MD direction dimension 31m of each extruded projection 31 is equal to or smaller than a central space 80y between a top-second joint portion 80 (described later) positioned on an MD direction one side of the extruded projection 31 and a top-second joint portion 80 positioned on the other side of the extruded projection 31 as illustrated in FIGS. 8 to 11. The lower limit is preferably about 0.9 times of the central space 80y, and for a diaper for infants, the MD direction dimension 31m is preferably about 2.7 to 9 mm. Similarly, a CD direction dimension 31c of each extruded projection 31 is equal to or smaller than a central space 80x between a top-second joint portion 80 positioned on a CD direction one side of the extruded projection 31 and a top-second joint portion 80 positioned on the other side of the extruded projection 31. The lower limit is preferably about 0.9 times of the central space 80x, and for a diaper for infants, the CD direction dimension 31c is preferably about 2.7 to 9 mm. In addition, a height 31z of the extruded projection 31 is preferably about 0.8 to 2 mm for a diaper for infants.

The "MD direction" and "CD direction" in the product refer to the "MD direction" and "CD direction" in a processing facility for the extruded projections 31, and one of the directions is the front-back direction and the other is the width direction. The MD direction in the product is the direction in which fibers of non-woven fabric in the top sheet 30 are oriented. The orientation direction of the fibers is the direction along which the fibers of the non-woven fabric are aligned. The orientation direction can be determined by a measurement method in conformity with a fiber orientation test method with zero-distance tensile strength of TAPPI standard method T481, or a simple measurement method for deciding the direction of fiber orientation from the ratio of tensile strengths in the front-back direction and the width direction, for example. In the illustrated example, as in most of absorbent article products, the front-back direction is the MD direction, and the width direction is the CD direction.

The arrangement spaces between the extruded projections 31 can be decided as appropriate. However, for a diaper for infants, in the case of a matrix arrangement as illustrated in FIGS. 8 and 9, each CD direction central space 31x in the MD direction columns of the CD direction adjacent extruded projections 31 is preferably about 3 to 10 mm, and each MD direction central space 31y in the CD direction columns of the MD direction adjacent extruded projections 31 is preferably about 3 to 10 mm. In the case of a staggered arrangement as illustrated in FIG. 10, each CD direction central space 31x in the MD direction columns of the CD direction adjacent extruded projections 31 is preferably about 3 to 10 mm, and each MD direction central space 31y in the CD direction columns of the MD direction adjacent extruded projections 31 is preferably about 3 to 10 mm.

The shape of the extruded projections 31 is preferably a circular dome, but may be an oval dome or a regular polygon dome. Since the extruded projections 31 are formed by extruding the top sheet 30 by embossing, the shape of the convex portions for use in the extruding process can be appropriately changed to obtain a desired shape.

(Top-Second Joint Portions)

Figure 9A:
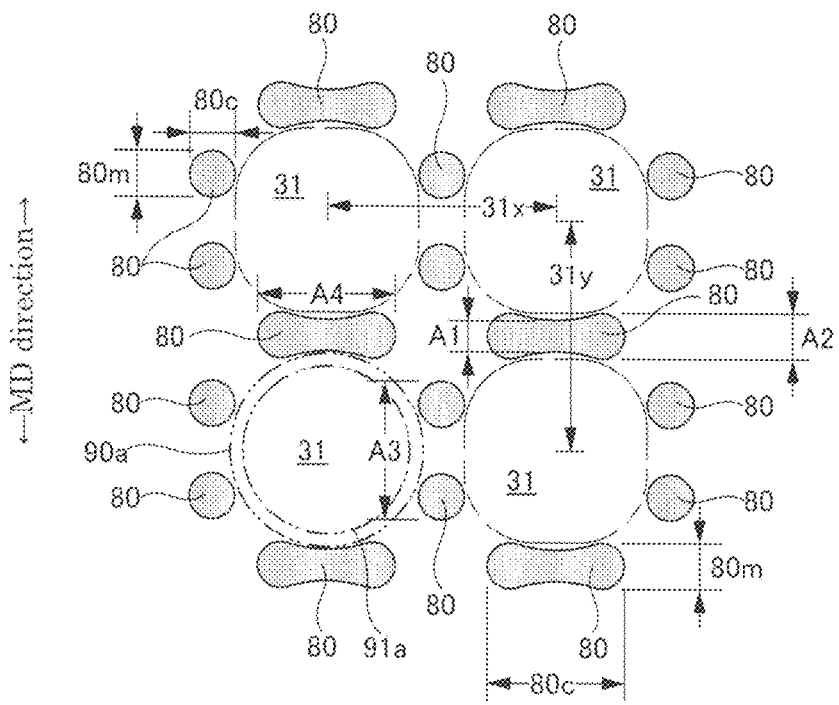
FIGS. 9(a) and 9(b) are enlarged plane views of joint patterns of top-second joint portions.
Figure 13:
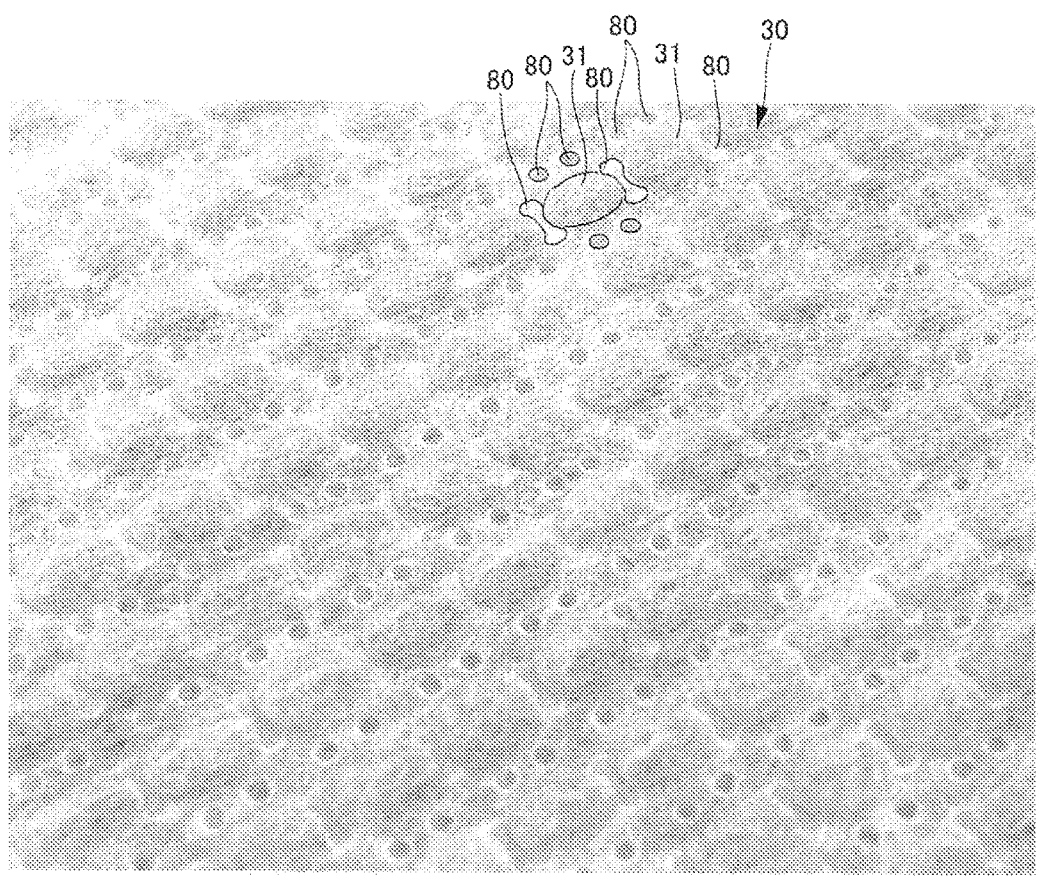
FIG. 13 is a photograph of a top sheet and second sheet assembly body in a perspective direction.
Figure 14:
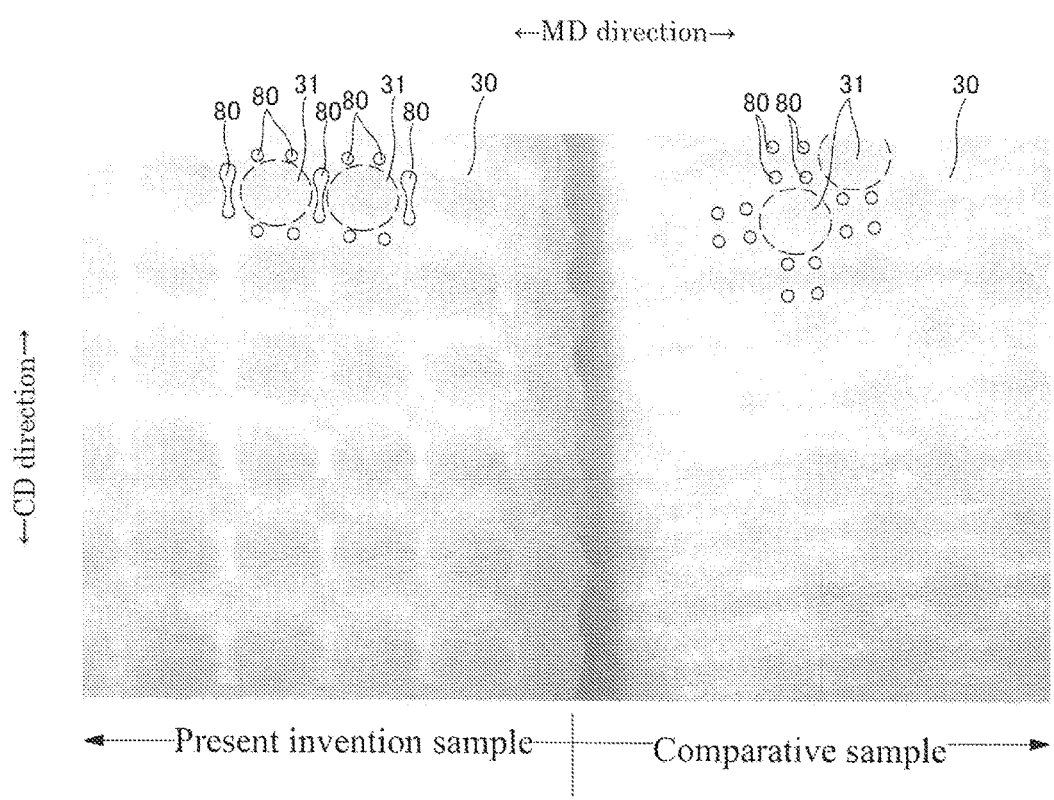
FIG. 14 shows comparison photographs obtained by shooting the surfaces of top sheets of a tape-type disposable diaper sample of the present invention and a comparison sample.

As illustrated in FIGS. 9 and 10, the portions between the extruded projections 31 adjacent in the width direction and the front-back direction are joined to the second sheet 40, thereby to form a large number of top-second joint portions 80 in a joint pattern intermittent in the width direction and the front-back direction. In addition, characteristically, in the joint pattern of the top sheet 30 and the second sheet 40, the top-second joint portions 80 are formed between the MD direction adjacent extruded projections 31 at CD direction central positions corresponding to the CD direction central portions of the adjacent extruded projections 31 and at lateral positions on the CD direction both sides of the central positions, and the MD direction joint ranges A1 and A2 are wider continuously or stepwise with increasing proximity from the central positions to the lateral sides (hereinafter, also called wrinkle preventive pattern). FIG. 13 is a photograph of a sample of assembly body of the top sheet 30 and the second sheet 40 in the pattern illustrated in FIG. 9(a). By employing the characteristic joint pattern between the MD direction adjacent extruded projections 31 in this manner, as apparent from the sample of the present invention illustrated in FIG. 14(a), even when vertical wrinkles occur at the time of formation of the extruded projections 31, the wrinkles can be smoothed out to the CD direction both sides, and removed or made less prominent without deforming the extruded projections 31 at the time of joining with the second sheet 40. In contrast to this, in the comparative sample having the top-second joint portions 80 not satisfying the foregoing conditions, a large number of MD direction wrinkles occurs with CD direction spaces left therebetween to deteriorate the appearance.

The length of a shortest portion A1 and the length of a longest portion A2 of the MD direction joint range can be decided as appropriate. However, the longest portion A2 is preferably about 1.1 to 2 times as long as the shortest portion A1.

Figure 15:
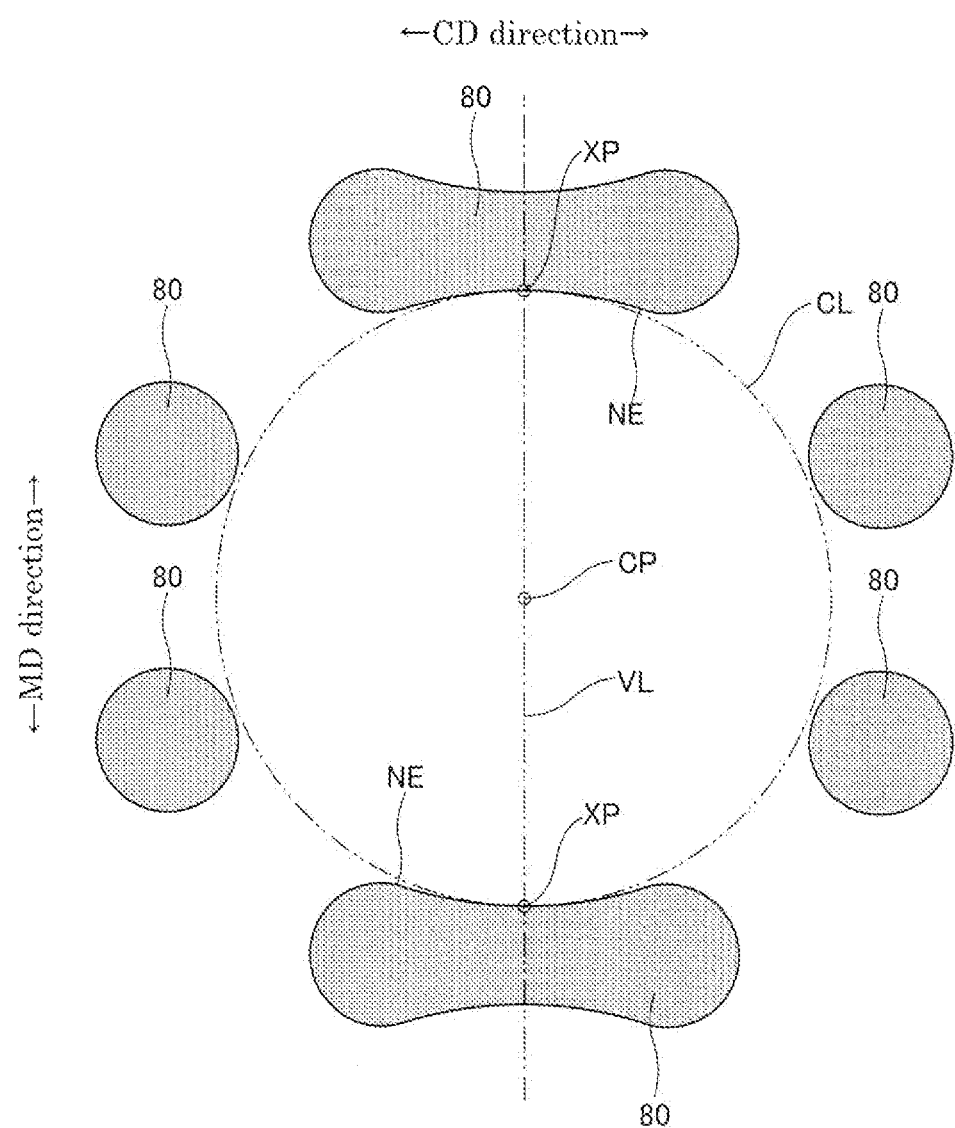
FIG. 15 is an enlarged plane view of a joint pattern of the top-second joint portions.

The degrees of a change in the MD direction joint ranges A1 and A2 can be decided as appropriate. However, as illustrated in FIG. 15, the top-second joint portions 80 are preferably positioned between the MD direction adjacent extruded projections 31 on a virtual arc CL that has a center CP (the MD direction and CD direction center) of the extruded projection 31 and passes through a cross point XP between a virtual central line VL passing through the center CP along the MD direction and a proximal edge NE of the top-second joint portion 80 or outside the virtual arc CL because the extruded projections 31 can be formed in a largely rounded shape (circular or rounded-corner square). In this case, the top-second joint portions 80 between the CD direction adjacent extruded projections 31 are also desirably arranged with the proximal edge on the virtual arc CL or outside the virtual arc CL. Although not illustrated, on the contrary, at least either of the top-second joint portions 80 between the MD direction adjacent extruded projections 31 and the top-second joint portions 80 between the CD direction adjacent extruded projections 31 may be positioned inside the virtual arc CL.

Figure 10A:
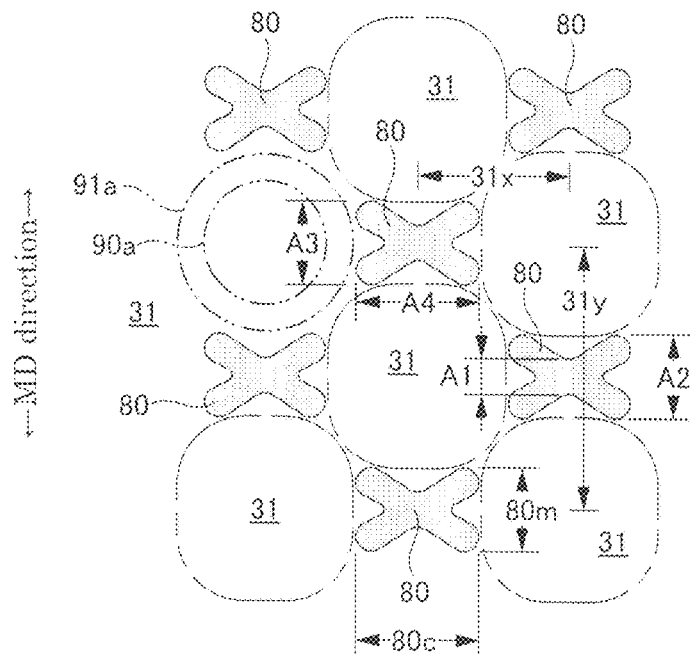
FIGS. 10(a) and 10(b) are enlarged plane views of joint patterns of the top-second joint portions.

There is no limitation on the wrinkle preventive pattern. However, as illustrated in FIGS. 9(a) and 10(a), the top-second joint portions 80 between the MD direction adjacent extruded projections 31 are formed as integral joint portions that extend continuously from the central position to the CD direction both sides and are longer in the MD direction continuously (or stepwise) with increasing proximity to the lateral sides, for example. The change in the MD direction length may be stepwise, but are desirably continuous to form the entirely gourd-shaped joint portions as in the illustrated example. The wrinkle preventive pattern by the integral top-second joint portions 80 is more excellent in the effect of preventing wrinkles than a wrinkle preventive pattern by a plurality of top-second joint portions 80 separated from each other as described later.

The dimensions and shape of the integral top-second joint portions 80 in the wrinkle preventive pattern can be decided as appropriate. However, the top-second joint portions 80 between the MD direction adjacent extruded projections 31 preferably has a horizontally long shape longer in the CD direction in which a MD direction length 80m of the top-second joint portions 80 is about 0.1 to 1 times as large as MD direction central space 31y in the CD direction columns of the MD direction adjacent extruded projections 31 (for example, 0.5 to 10 mm for a diaper for infants), and a CD direction length 80c of the top-second joint portions 80 is about 0.3 to 1 times as large as CD direction central space 31x in the MD direction columns of the CD direction adjacent extruded projections 31 (for example, 1 to 10 mm for a diaper for infants).

Figure 9B:
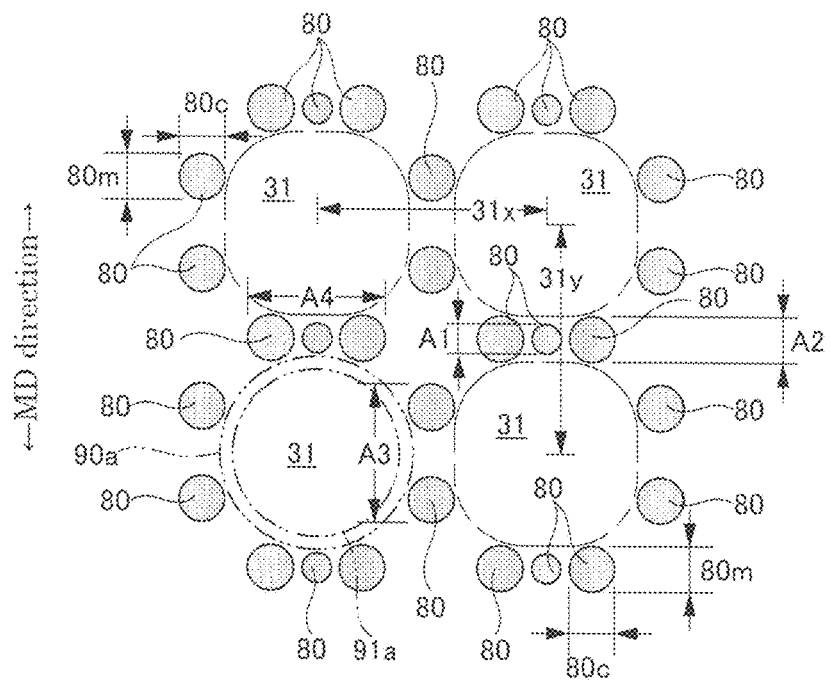
Figure 10B:
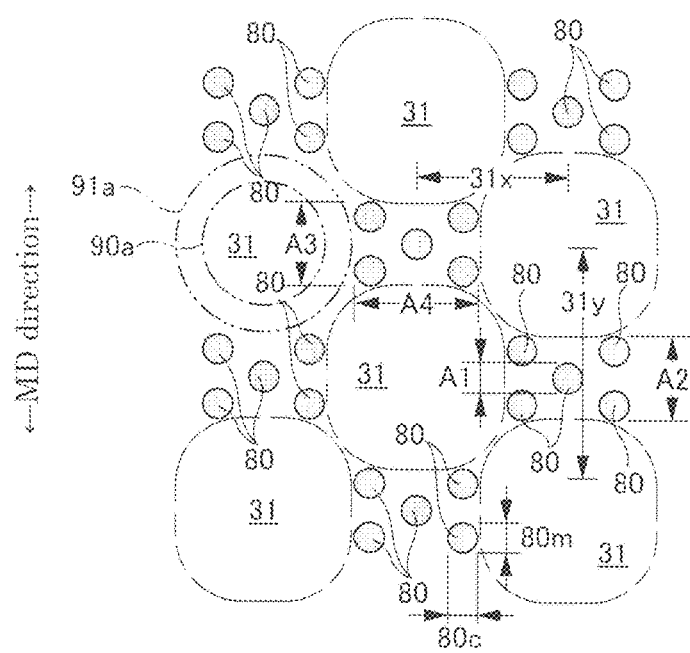
Figure 11:
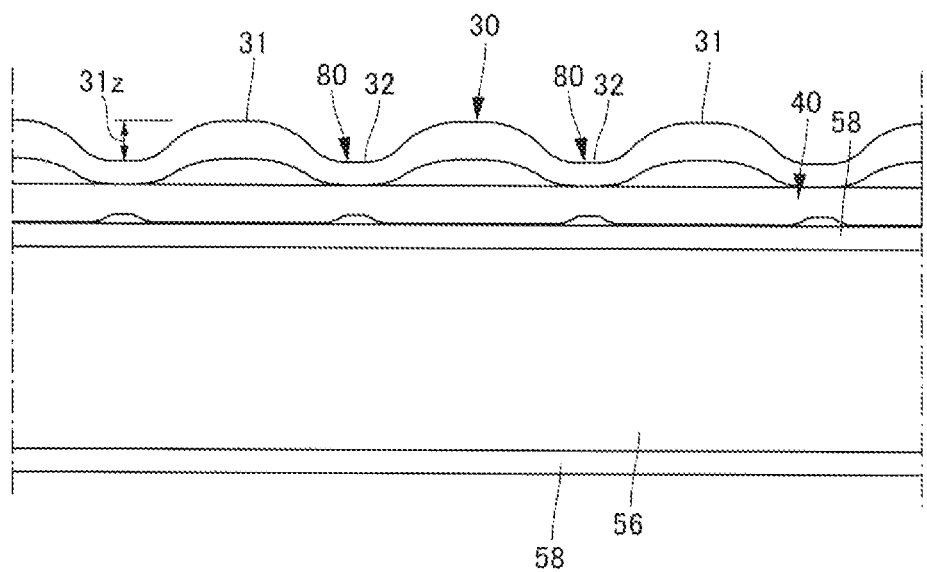
FIG. 11 is a cross-sectional view of main parts such as the top-second joint portions.

The wrinkle preventive pattern can also be formed as illustrated in FIGS. 9(b) and 10(b) by providing the top-second joint portions 80 so as to be separated from each other at the central positions and the lateral positions between the MD direction adjacent extruded projections 31, and increasing the number of the top-second joint portions 80 in the MD direction stepwise with increasing proximity from the central position to the lateral sides. Although not illustrated, instead of changing the number of the top-second joint portions 80 in the MD direction, the length of the top-second joint portions 80 may be changed, and the change may be continuous. In the case of the wrinkle preventive pattern by the foregoing integral top-second joint portions 80, there is the possibility that the top sheet 30 is decreased in permeability and flexibility. Meanwhile, the wrinkle preventive pattern formed by the plurality of top-second joint portions 80 separated from each other can reduce the possibility and fully exert the effect of preventing wrinkles.

The dimensions and shape of the wrinkle preventive pattern having the plurality of top-second joint portions 80 separated from each other can be decided as appropriate. However, the top-second joint portions 80 are preferably dot-like joint portions in which the MD direction length 80m of the individual top-second joint portions 80 between the MD direction adjacent extruded projections 31 is about 0.1 to 0.4 times as large as the MD direction central space 31y in the CD direction columns of the MD direction adjacent extruded projections 31 (for example, 0.5 to 3 mm for a diaper for infants) and the CD direction length 80c of the individual top-second joint portions 80 is about 0.1 to 0.4 times as large as the CD direction central space 31x in the MD direction columns of the CD direction adjacent extruded projections 31 (for example, 0.5 to 3 mm for a diaper for infants).

When the extruded projections 31 are formed in a staggered pattern as illustrated in FIG. 10, the spaces between the CD direction adjacent extruded projections 31 are also the spaces between the MD direction adjacent extruded projections 31. Accordingly, the top-second joint portions 80 are provided in the same manner as those between the MD direction adjacent extruded projections 31. Meanwhile, when the extruded projections 31 are formed in a matrix pattern as illustrated in FIG. 9, separately from the top-second joint portions 80 between the MD direction adjacent extruded projections 31, the top-second joint portions 80 are intermittently provided between the CD direction adjacent extruded projections 31. There is no particular limitation on the pattern of the top-second joint portions 80. However, the dot-like top-second joint portions 80 are preferably arranged with front-back space therebetween. One MD direction column of the top-second joint portions 80 may be provided at the middle position between the CD direction adjacent extruded projections 31 as in the illustrated example, or a plurality of MD direction columns of the top-second joint portions 80 may be provided with CD direction space left therebetween. There is no particular limitation on the dimensions of the dot-like top-second joint portions 80. However, the MD direction length 80m is preferably about 0.1 to 0.4 times as large as the MD direction central space 31y in the CD direction columns of the MD direction adjacent extruded projections 31 (for example, 0.5 to 3 mm for a diaper for infants), and the CD direction length 80c is preferably about 0.1 to 0.4 times as large as the CD direction central space 31x in the MD direction columns of the CD direction adjacent extruded projections 31 (for example, 0.5 to 3 mm for a diaper for infants).

The top-second joint portions 80 are formed in a joint pattern intermittent in the width direction and the front-back direction, and the space therebetween in the directions can be decided as appropriate. For example, a CD direction joint range A3 of the top-second joint portions 80 between the MD direction adjacent extruded projections 31 is preferably about 0.3 to 1 times as large as the CD direction central space 31x in the MD direction columns of the CD direction adjacent extruded projections 31 (for example, 1 to 10 mm for a diaper for infants), and an MD direction joint range A4 of the top-second joint portions 80 between the CD direction adjacent extruded projections 31 is preferably about 0.3 to 1 times as large as the MD direction central space 31y in the CD direction columns of the MD direction adjacent extruded projections 31 (for example, 1 to 10 mm for a diaper for infants). When the CD direction joint range A3 and the MD direction joint range A4 are too wide, the top-second joint portions 80 are substantially continuous in the CD direction and the MD direction, which may reduce the permeability and flexibility of the top sheet 30.

Example of a Method for Producing the Disposable Diaper

Figure 12:
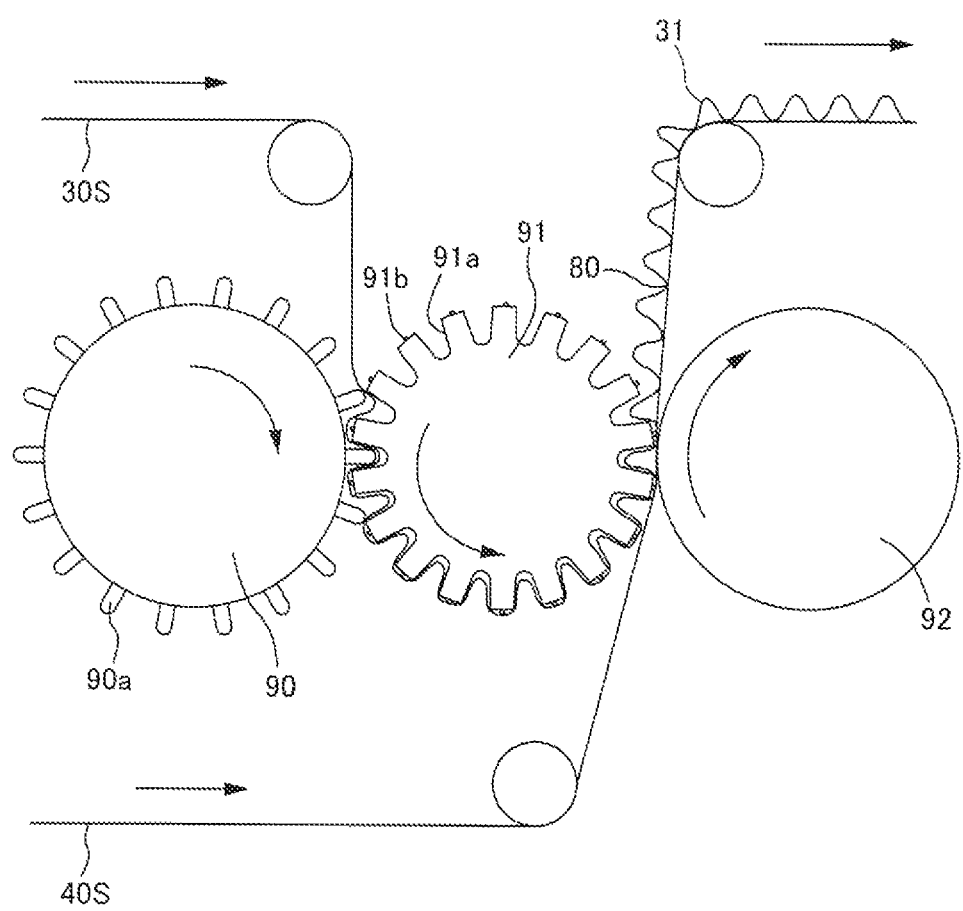
FIG. 12 is an illustrative diagram of an assembly facility for the top sheet and the second sheet.

FIG. 12 illustrates an assembly facility for the top sheet 30 and the second sheet 40 for producing the foregoing disposable diaper. Specifically, the facility includes: a push roll 90 with a large number of push convex portions 90a formed on the peripheral surface in the arrangement pattern of the extruded projections 31 described above; a concave roll 91 that is opposed to the push roll 90, and has concave portions 91a corresponding to the push convex portions 90a and joint convex portions 91b provided between the concave portions 91a in the arrangement pattern of the top-second joint portions 80 described above; and a joint roll 92 opposed to the concave roll 91. The shape of the convex portions in the push roll 90 can be decided as appropriate. However, the convex portions preferably have a truncated frustum shape with a cross section adapted to the shape of the extruded projections 31 to be formed (for example, circle, oval, regular polygon, or the like). The concave portions 91a in the concave roll 91 may be "open holes" without bottom surfaces into which the convex portions can enter as far as they have projections, and the "concave portions 91a" in the present invention also include such "open holes". The dimensions and shape of the extruded projections 31 formed by the push roll 90 and the concave roll 91 almost correspond to the dimensions and shapes of the push convex portions and the concave portions 91a as illustrated by two-dot chain lines in FIGS. 9 and 10.

In the process, non-woven fabric 30S to be the top sheet 30 is conveyed by drawing from the downstream side and sandwiched between the push roll 90 and the concave roll 91, and the non-woven fabric 30S is processed by embossing such that convex portions in the push roll 90 are pushed into the concave portions 91a in the concave roll 91, thereby forming the protruded projections 31.

After that, the non-woven fabric 30S with the extruded projections 31 is wound around the concave roll 91 and guided in that state. In the course of guiding, a material 40S for the second sheet 40 is fed by drawing from the downstream side to the outside of the non-woven fabric to be the top sheet 30. Then, the non-woven fabric 30S to be the top sheet 30 and the material 40S for the second sheet 40 are sandwiched between the concave roll 91 and the joint roll 92, and are thermally pressed and adhered between the joint convex portions 91b of the concave roll 91 and the peripheral surface of the joint roll 92 to form the top-second joint portions 80 in the joint pattern described above, thereby producing an assembly body of the top sheet 30 and the second sheet 40. The joint pattern is as described above, and duplicate descriptions will be omitted here. The joint means may be thermal pressing and adhesion or adhesion by heat sealing or a hot-melt adhesive. The assembly body of the top sheet 30 and the second sheet 40 is assembled into the absorber or the like by a publicly known method to produce the disposable diaper.

In the processing method by which the non-woven fabric 30S is joined to the material for the second sheet 40 immediately after the formation of the extruded projections 31 and before wrinkles are not substantially absorbed, the wrinkles are likely to remain in the product. Accordingly, the joint pattern of the top-second joint portions 80 is preferably employed. As a matter of course, any processing facility other than the foregoing three-roll processing facility may be used to form the top-second joint portions 80 after the formation of the extruded projections 31 by embossing. In the illustrated example, the non-woven fabric to be the top sheet 30 is fed directly to the position of engagement between the push roll 90 and the concave roll 91. Alternatively, the non-woven fabric to be the top sheet 30 may be fed and wound around only the push roll 90 from the direction of tangent to the peripheral surface of the push roll 90, sandwiched between the push roll 90 and the concave roll 91, and then moved to the peripheral surface of the concave roll 91.

Descriptions of the Terms Used Herein

Unless otherwise specified herein, the terms used herein have the meanings described below.
(Gel Strength)
The gel strength is measured in such a manner as described below. That is, a high-absorbent polymer of 1.0 g is added to an artificial urine of 49.0 g (urea: 20 wt %, salt: 8 wt %, calcium chloride dihydrate: 0.3 wt %, magnesium oxide heptahydrate: 0.8 wt %, and pure water: 70.01 wt %), and then the mixture is agitated with a stirrer. The resultant gel is left stand for three hours in a constant temperature and humidity chamber at 40° C. and 60% RH, and then returned to a room-temperature environment. Then, the gel strength is measured by a curd meter (Curdmeter-MAX ME-500 produced by I. Techno Engineering Co., Ltd.).
(Basis Weight)
The basis weight is measured as described below. A specimen or a test piece is preliminarily dried and left stand in a test room or a test device in a standard state (a place of test shall be at a temperature of 20±5° C. and a relative humidity of 65% or less) until reaching a constant weight. The preliminary drying refers to turning the specimen or the test piece to a constant weight in an environment at a relative humidity of 10 to 25% and a temperature not exceeding 50° C. The preliminary drying is not necessary for fibers with an official moisture regain of 0.0%. The test piece of the constant weight is cut into a 200 mm×250 mm (±2 mm) specimen by the use of a basis weight plate (200 mm×250 mm±2 mm). The weight of the specimen is measured and the measured value is multiplied by 20 to determine the weight per square meter as a basis weight.
(Thickness)
The thickness is automatically measured by an automated thickness gauge (KES-G5 handy compression measurement program) on the conditions that the load is 10 gf/cm$^2$ and the pressure area is 2 cm$^2$.
(Directions)
The "front-back direction (longitudinal direction)" means the direction of connecting the ventral side (front side) and the dorsal side (back side). The "width direction" means the direction orthogonal to the front-back direction (horizontal direction). The "up-down direction" means the direction orthogonal to the width direction when the diaper is worn, that is, when the diaper is folded double at the crotch portion such that the ventral side part and the dorsal side part overlap.
(Extension Ratio)
The "extension ratio" takes a value relative to the natural length of 100%.

If there is no description on environmental conditions in testing or measurements, the testing or the measurements shall be conducted in a test room or within a device under a normal state (a place of test shall be at temperatures of 20±5° C. and relative humidity of 60% or less).

REFERENCE SIGNS LIST

A1 and A2 MD direction joint range
11 Liquid impervious sheet
12 Outer sheet
12T Target sheet
13 Fastening tape
13A Engage part
13B Tape main part
13C Tape attachment part
30 Top sheet
31 Extruded projection
40 Second sheet
50 Absorbent element
56 Absorber
58 Wrapping sheet
60 Side-part three-dimensional gather
62 Gather sheet
70 Dorsal side elastic waist sheet
80 Top-second joint portion
90 Push roll
90a Push convex portion
91 Concave roll
91a Concave portion
91b Joint convex portion
92 Joint roll

The invention claimed is:
1. A method for producing an absorbent article including:
an absorber,
a liquid pervious top sheet formed from non-woven fabric covering a front side of the absorber, and
a second sheet stuck to a back surface of the top sheet, the top sheet having a large number of extruded projections formed by being extruded from the back side to the front side with space left therebetween in a width direction and a front-back direction, and portions between the extruded projections adjacent in the width direction and the front-back direction in the top sheet being joined to the second sheet to form a large number of top-second joint portions in a joint pattern intermittent in the width direction and the front-back direction, wherein, in assembling the top sheet and the second sheet, the method comprises:

while conveying the non-woven fabric to be the top sheet, forming the extruded projections by embossing; and placing a material for the second sheet on the back surface of the non-woven fabric with the extruded projections, and joining the non-woven fabric and the material for the second sheet in the joint pattern, wherein the top-second joint portions are formed between MD direction adjacent extruded projections, are integral joint portions that extend continuously from CD direction central positions corresponding to CD direction central portions of the adjacent extruded projections to the CD direction both sides, and become longer continuously or stepwise in the MD direction with increasing proximity to the lateral sides.

2. A method for producing an absorbent article including:
an absorber,
a liquid pervious top sheet formed from non-woven fabric covering a front side of the absorber, and
a second sheet stuck to a back surface of the top sheet, the top sheet having a large number of extruded projections formed by being extruded from the back side to the front side with space left therebetween in a width direction and a front-back direction, and portions between the extruded projections adjacent in the width direction and the front-back direction in the top sheet being joined to the second sheet to form a large number of top-second joint portions in a joint pattern intermittent in the width direction and the front-back direction, wherein, in assembling the top sheet and the second sheet, the method comprises:

while conveying the non-woven fabric to be the top sheet, forming the extruded projections by embossing; and placing a material for the second sheet on the back surface of the non-woven fabric with the extruded projections, and joining the non-woven fabric and the material for the second sheet in the joint pattern, wherein the top-second joint portions are formed between the MD direction adjacent extruded projections at CD direction central positions corresponding to CD direction central portions of the adjacent extruded projections and at lateral positions on the CD direction both sides of the central positions so as to be separated from each other, and the number or length of the top-second joint portions are larger or longer continuously or stepwise in the MD direction with increasing proximity to the lateral sides.

3. The method for producing an absorbent article according to claim 1, comprising:

using a push roll with a large number of push convex portions formed in an arrangement pattern of the extruded projections on a peripheral surface, a concave roll that is opposed to the push roll, and has concave portions corresponding to the push convex portions and joint convex portions provided between the concave portions, and a joint roll opposed to the concave roll;

while conveying the non-woven fabric to be the top sheet, sandwiching the non-woven fabric between the push roll and the concave roll, pushing the convex portions in the push roll into the concave portions in the concave roll to form the extruded projections, and then while winding the non-woven fabric to be the top sheet around the concave roll and guiding the same, feeding the material for the second sheet to the outside of the non-woven fabric to be the top sheet, sandwiching the non-woven fabric to be the top sheet and the material for the second sheet between the concave roll and the joint roll, and thermally pressing and adhering the non-woven fabric to be the top sheet and the material for the second sheet between the joint convex portions of the concave roll and the peripheral surface of the joint roll to form the top-second joint portions.

* * * * *